(12) United States Patent
Lim et al.

(10) Patent No.: US 11,036,465 B2
(45) Date of Patent: Jun. 15, 2021

(54) SLEEP DETECTION SYSTEM FOR WEARABLE AUDIO DEVICE

(71) Applicant: Bose Corporation, Framingham, MA (US)

(72) Inventors: Chiao Woon Lim, Singapore (SG); Lee Zamir, Cambridge, MA (US)

(73) Assignee: BOSE CORPORATION, Framingham, MA (US)

( * ) Notice: Subject to any disclaimer, the term of this patent is extended or adjusted under 35 U.S.C. 154(b) by 7 days.

(21) Appl. No.: 16/665,505

(22) Filed: Oct. 28, 2019

(65) Prior Publication Data
US 2021/0124552 A1 Apr. 29, 2021

(51) Int. Cl.
| | |
|---|---|
| G06F 3/16 | (2006.01) |
| H04R 29/00 | (2006.01) |
| G08B 3/10 | (2006.01) |
| G08B 21/18 | (2006.01) |
| A61M 21/02 | (2006.01) |
| A61M 21/00 | (2006.01) |

(52) U.S. Cl.
CPC ............ *G06F 3/165* (2013.01); *A61M 21/02* (2013.01); *G08B 3/10* (2013.01); *G08B 21/182* (2013.01); *H04R 29/001* (2013.01); *A61M 2021/0027* (2013.01); *A61M 2021/0083* (2013.01); *A61M 2230/63* (2013.01)

(58) Field of Classification Search
CPC ............ G06F 3/16; G06F 3/162; G06F 3/165; A61M 21/02; A61M 2021/0027; A61M 2021/0083; A61M 2230/83; G08B 3/10; G08B 21/182; H04R 29/00; H04R 29/001; H04R 29/002; H04R 29/007

USPC ...... 381/58, 104, 107, 109; 700/94; 340/575
See application file for complete search history.

(56) References Cited

U.S. PATENT DOCUMENTS

| | | |
|---|---|---|
| 4,150,262 A | 4/1979 | Ono |
| 4,297,685 A | 10/1981 | Brainard, II |
| 4,334,315 A | 6/1982 | Ono et al. |
| 4,374,382 A | 2/1983 | Markowitz |
| 4,588,867 A | 5/1986 | Konomi |
| 4,654,883 A | 3/1987 | Iwata |
| 4,791,673 A | 12/1988 | Schreiber |
| 6,094,492 A | 7/2000 | Boesen |
| 6,408,081 B1 | 6/2002 | Boesen |
| 6,920,229 B2 | 7/2005 | Boesen |
| 7,209,569 B2 | 4/2007 | Boesen |

(Continued)

FOREIGN PATENT DOCUMENTS

EP 06711115 B1 3/2002

*Primary Examiner* — Xu Mei
(74) *Attorney, Agent, or Firm* — Hoffman Warnick LLC

(57) ABSTRACT

Various aspects include approaches for controlling audio playback based upon a detected user sleep state. In one implementation, a computer-implemented method of controlling playback of an audio file at a wearable audio device includes: receiving a first indicator about movement or a position of an audio gateway over a period; receiving a second indicator about movement or position of the wearable audio device over the period, wherein the wearable audio device is separate from the audio gateway; and in response to the first indicator deviating from the second indicator by less than a threshold for the period, inserting a marker in the audio file that enables a user to revert back to the playback at a time of the marker.

20 Claims, 3 Drawing Sheets

(56) References Cited

U.S. PATENT DOCUMENTS

| | | | | |
|---|---|---|---|---|
| 8,243,946 | B2* | 8/2012 | Burge | H04R 1/1041 |
| | | | | 381/74 |
| 10,194,259 | B1* | 1/2019 | Martin | H04S 7/304 |
| 10,635,796 | B2* | 4/2020 | Tian | G06F 1/1694 |
| 2003/0144918 | A1* | 7/2003 | Novelli | G06Q 20/123 |
| | | | | 700/94 |
| 2014/0150002 | A1* | 5/2014 | Hough | H04N 21/2668 |
| | | | | 725/9 |
| 2016/0098138 | A1* | 4/2016 | Park | G06F 1/163 |
| | | | | 345/173 |
| 2016/0173982 | A1* | 6/2016 | Anderson | H04R 3/00 |
| | | | | 381/119 |
| 2017/0315675 | A1* | 11/2017 | Lewis | H04N 21/44218 |

\* cited by examiner

SLEEP DETECTION SYSTEM FOR WEARABLE AUDIO DEVICE

TECHNICAL FIELD

This disclosure generally relates to audio devices. More particularly, the disclosure relates to controlling audio device functions based upon a detected sleep state of a user.

BACKGROUND

Given increased network connectivity, data transmission speeds and the prevalence of personal audio devices, long form audio content is becoming increasing popular and accessible. Podcasts, audio books, audio periodicals and other forms of long-form audio can provide immersive user experiences without excessive screen time. However, the relaxing nature of long form audio content also causes some users to doze off to sleep during playback. In these cases, it is difficult for users to efficiently resume playback at the desired time in a playback file or stream. Additionally, in the case of relaxation-based long form audio content such as meditation audio playback, calming guides or sleep aid audio playback, knowing a user's sleep state can be beneficial in controlling playback and other device functions.

SUMMARY

All examples and features mentioned below can be combined in any technically possible way.

Various implementations of the disclosure include approaches for controlling audio playback, for example, based upon detected user sleep state.

In some particular aspects, a computer-implemented method of controlling playback of an audio file at a wearable audio device includes: receiving a first indicator about movement or a position of an audio gateway over a period; receiving a second indicator about movement or position of the wearable audio device over the period, where the wearable audio device is separate from the audio gateway; and in response to the first indicator deviating from the second indicator by less than a threshold for the period, inserting a marker in the audio file that enables a user to revert back to the playback at a time of the marker.

In other particular aspects, a wearable audio device includes: a sensor for generating a first indicator about movement or a position of the wearable audio device over a period; at least one transducer for playing back an audio file; and a controller coupled with the sensor and the at least one transducer, the controller configured to: receive the first indicator about movement or the position of the wearable audio device over a period; receive a second indicator about movement or a position of an audio gateway in communication with the wearable audio device over the period, where the wearable audio device is separate from the audio gateway; and in response to the first indicator deviating from the second indicator by less than a threshold for the period, inserting a marker in the audio file that enables a user to revert back to the playback at a time of the marker In additional particular aspects, a system includes: an audio gateway having a first sensor for detecting at least one of motion or a position of the audio gateway; and a wearable audio device separate from and communicably coupled with the audio gateway for playing back an audio file sent from the audio gateway, the wearable audio device including a second sensor for detecting at least one of motion or a position of the wearable audio device, where a controller at one of the audio gateway or the wearable audio device is configured to: receive a first indicator about movement or the position of the audio gateway over a period; receive a second indicator about movement or the position of the wearable audio device over the period; and in response to the first indicator deviating from the second indicator by less than a threshold for the period, insert a marker in the audio file that enables a user to revert back to the playback at a time of the marker.

Implementations may include one of the following features, or any combination thereof.

In certain implementations, the marker indicates the time in the playback of the audio file at which the movement or position of the audio gateway and the movement or position of the wearable audio device are approximately in sync.

In particular cases, the first indicator and the second indicator each comprise a plurality of indicators representing a rolling average of the movement or position of the audio gateway and the wearable audio device over the period.

In some aspects, the method further includes switching playback of the audio file to a distinct audio file in response to the first indicator deviating from the second indicator by less than the threshold, where the distinct audio file comprises a white noise audio file or a sleep track.

In particular cases, the first indicator about movement or position of the audio gateway is received from an inertial measurement unit (IMU) located at the audio gateway, and the second indicator about movement or position of the wearable audio device is received from an IMU located at the wearable audio device, where each IMU includes at least one of: an accelerometer, a gyroscope or a magnetometer.

In certain implementations, the method further includes playing an alarm at the wearable audio device in response to the first indicator deviating from the second indicator by less than the threshold.

In some aspects, the method further includes powering down the wearable audio device or disabling an application controlling playback of the audio file in response to the first indicator deviating from the second indicator by less than the threshold.

In particular implementations, the audio gateway includes a smart device that is configured to be worn or otherwise carried by a user.

In certain cases, the threshold defines approximately synchronized movement or position change between the wearable audio device and the audio gateway such that the user is estimated to be asleep when the first indicator deviates from the second indicator by less than the threshold for the period.

In some aspects, the period is at least approximately 30 seconds.

Two or more features described in this disclosure, including those described in this summary section, may be combined to form implementations not specifically described herein.

The details of one or more implementations are set forth in the accompanying drawings and the description below. Other features, objects and advantages will be apparent from the description and drawings, and from the claims.

Figure 1:
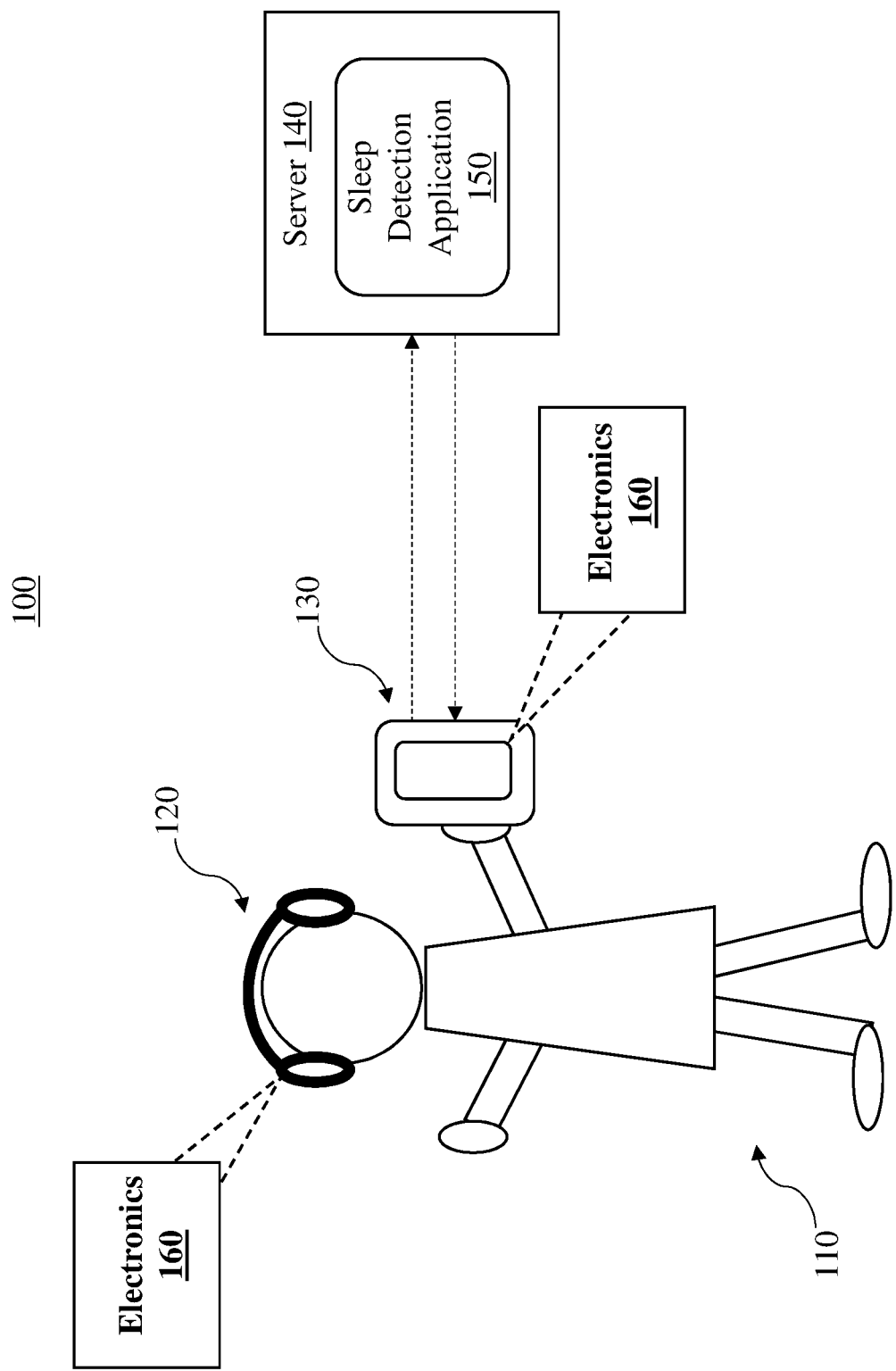
FIG. 1 shows an illustrative environment for performing sleep detection functions according to various implementations.

It is noted that the drawings of the various implementations are not necessarily to scale. The drawings are intended to depict only typical aspects of the disclosure, and therefore should not be considered as limiting the scope of the invention. In the drawings, like numbering represents like elements between the drawings.

DETAILED DESCRIPTION

As noted herein, various aspects of the disclosure generally relate to device control based on user activity detection. More particularly, aspects of the disclosure relate to controlling audio device functions based upon a detected sleep state of a user.

Commonly labeled components in the FIGURES are considered to be substantially equivalent components for the purposes of illustration, and redundant discussion of those components is omitted for clarity.

Aspects and implementations disclosed herein may be applicable to a wide variety of speaker systems, such as wearable audio devices in various form factors, such as headphones (whether on or off ear), headsets, watches, eyeglasses, neck-worn speakers, shoulder-worn speakers, body-worn speakers, audio sleeping aids, etc. Unless specified otherwise, the term wearable audio device, as used in this document, includes headphones and various other types of personal audio devices such as head, shoulder or body-worn acoustic devices that include one or more acoustic drivers to produce sound. Some particular aspects disclosed may be particularly applicable to personal (wearable) audio devices such as in-ear headphones (also referred to as earbuds), eyeglasses or other head-mounted audio devices.

While described by way of example, wearable audio devices such as in-ear headphones (e.g., earbuds), audio accessories or clothing (e.g., audio hats, audio visors, audio jewelry, neck-worn speakers or audio eyeglasses (also referred to as eyeglass headphones) herein, the wearable audio devices disclosed herein can include additional features and capabilities. That is, the wearable audio devices described according to various implementations can include features found in one or more other wearable electronic devices, such as smart glasses, smart watches, etc. These wearable audio devices can include additional hardware components, such as one or more cameras, location tracking devices, microphones, etc., and may be capable of voice recognition, visual recognition, and other smart device functions. The description of wearable audio devices included herein is not intended to exclude these additional capabilities in such a device.

Various implementations include systems and approaches for controlling audio playback at a wearable audio device based upon a detected user's sleep state. FIG. 1 illustrates an example environment 100, including a user 110 and an audio device (e.g., a wearable audio device) 120. While the audio device 120 is illustrated in this example as a wearable audio device (e.g., headphones, earphones, audio glasses, open-ear audio devices, shoulder-worn speakers or wearable speakers), the audio device 120 can include any conventional portable audio device such as a portable speaker, portable smart speaker, etc. In some implementations, the audio device 120 is connected with an audio gateway 130. In various implementations, the audio gateway 130 includes a smart device, e.g., a portable smart device. In additional implementations, the audio device 120 can have integrated smart device capabilities (e.g., communications and data processing). Both the audio device 120 and the audio gateway 130 can include processing components and communications components, for communicating with one another and/or other devices in the environment 100. In certain cases, the communications components include one or more wireless transceivers, e.g., to communicate with one or more smart devices in the environment 100. The wireless transceivers can also be used to communicate with a server 140 hosting a mobile application that is running on the audio gateway 130 and/or the audio device 120, for example, a sleep detection application 150. The server 140 can include a cloud-based server, a local server or any combination of local and distributed computing components capable of executing functions described herein. In various particular implementations, the server 140 is a cloud-based server configured to host the sleep detection application 150, e.g., running on the audio gateway 130. According to some implementations, the sleep detection application 150 is downloaded to the user's audio device 120 and/or audio gateway 130 in order to enable functions described herein. In certain cases, the server 140 is connected with a computing device that enables coding of the sleep detection application 150, e.g., by a software developer or other programmer.

Figure 2:
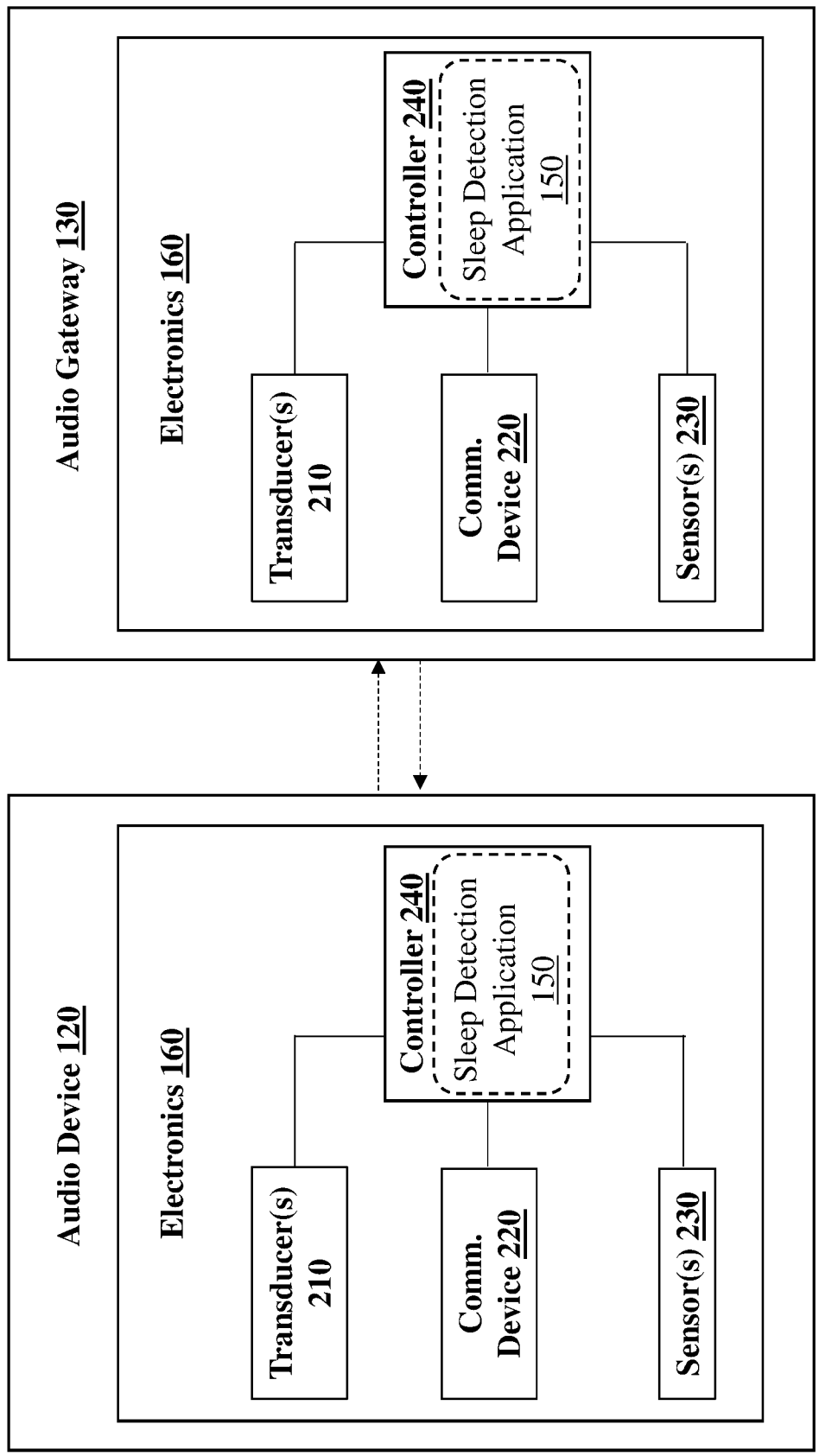
FIG. 2 is a schematic depiction of select electronics substantially contained in devices depicted in FIG. 1.

The audio device 120 and/or the audio gateway (e.g., smart device) 130 each include various electronics 160, illustrated in simplified form in the system diagram in FIG. 2. For example, electronics 160 can include transducers 210 (e.g., at least one electroacoustic transducer for producing an acoustic output), communications (comm.) devices 220 (e.g., wireless transceivers), and a set of sensors 230. Components in electronics 160 can be connected or otherwise centrally managed by a controller 240.

In various implementations, the controller 240 in the audio device 120 and/or the audio gateway 130 can include a processor (e.g., including a logic engine) to execute instructions for detecting (e.g., inferring) a user's sleep state and controlling device functions. In some cases, a memory is coupled with the processor to store the instructions. In other implementations, the processor can otherwise access the instructions, e.g., from a remote storage system such as the server 140 (FIG. 1). When executed by the processor in the controller 240, the instructions cause the processor to detect (or, infer) a user's sleep state and take a prescribed action according to that inference. In some cases, the instructions are part of the sleep detection application 150, which can be accessed via the server 140 or locally stored in memory, e.g., at the controller 240 or in another storage system in the audio device 120 and/or the audio gateway 130. The memory at the audio device 120 and/or the audio gateway 130 can include, for example, flash memory and/or non-volatile random access memory (NVRAM). In some implementations, instructions (e.g., software such as the sleep detection application 150) are stored in an information carrier. The instructions, when executed by one or more processing devices, perform one or more processes, such as those described elsewhere herein. The instructions can also be stored by one or more storage devices, such as one or more (e.g. non-transitory) computer- or machine-readable mediums (for example, the memory, or memory on the processor). As described herein, the memory can include instructions, or the processor can otherwise access instructions for infer a user's sleep state and take a prescribed action according to various particular implementations. It is understood that portions of the memory (e.g., instructions) can also be stored in a remote location or in a distributed location, and can be fetched or otherwise obtained by the processor (e.g., via any communications protocol described herein) for execution.

Additional components included in electronics 160 and not necessarily depicted can include power source(s), signal amplification and other digital signal processing (DSP) hardware and/or software, active noise reduction (ANR) and/or controllable noise cancelling (CNC) systems, input/output (I/O) devices, displays and/or user interfaces (UIs), etc. It is understood that the electronics 160 at the audio gateway 130 can include various additional components not included at the audio device 120, for example, components enabling smart device functions, audio gateway functions and additional processing.

In any case, the controller 240 is configured to use data from sensor(s) 230 at both the audio device 120 and the audio gateway 130 to infer the sleep state for the user 110 (FIG. 1), and take a prescribed action based upon that inferred sleep state. In various implementations, the sensor(s) 230 includes at least one MEMS device that combines a multi-axis accelerometer, gyroscope, and/or magnetometer (sometimes referred to as an IMU or inertial measurement unit). In particular cases, the sensor(s) 230 (e.g., IMU(s)), are configured to send sensor signals (e.g., motion or position indication signals) to controller(s) 240 on a continuous basis, or in particular cases, in response to movement detected by the sensor(s) 230 (e.g., as detected by a multi-axis accelerometer, gyroscope, and/or magnetometer in an IMU). According to some implementations, the sensor(s) 230 detects both relative movement and absolute position of the audio device 120 and/or audio gateway 130. While orientation tracking and/or motion detection using an IMU is described according to various implementations, additional or alternative sensors can be used to provide feedback about user orientation and/or movement, e.g., optical tracking systems such as cameras or LIDAR systems, and/or acoustic-based tracking systems.

In particular cases, each respective IMU is configured to detect changes in the physical location of the audio device 120 and the audio gateway 130, and provide updated sensor data to the controller(s) 240 in order to indicate a change in the relative location of the devices. The respective IMUs are also configured to detect the orientation of the audio device 120 and the audio gateway 130, e.g., a direction of the audio device 120 and the audio gateway 130, or a change in the orientation of audio device 120 and the audio gateway 130 such as a turning, flipping or rotating of a certain number of degrees. In these examples, the IMU may be particularly useful in detecting changes in orientation.

In any case, the IMU (and/or additional sensors 230) can provide sensor data to the controller(s) 240 about the location and/or orientation of the audio device 120 and the audio gateway 130. While sensors 230 located at the audio device 120 and audio gateway 130 are described according to various implementations, it is understood that the electronics 160 can also include one or more optical or visual detection systems located at another connected device configured to detect relative changes in location and/or orientation of the audio device 120 and the audio gateway 130.

Figure 3:
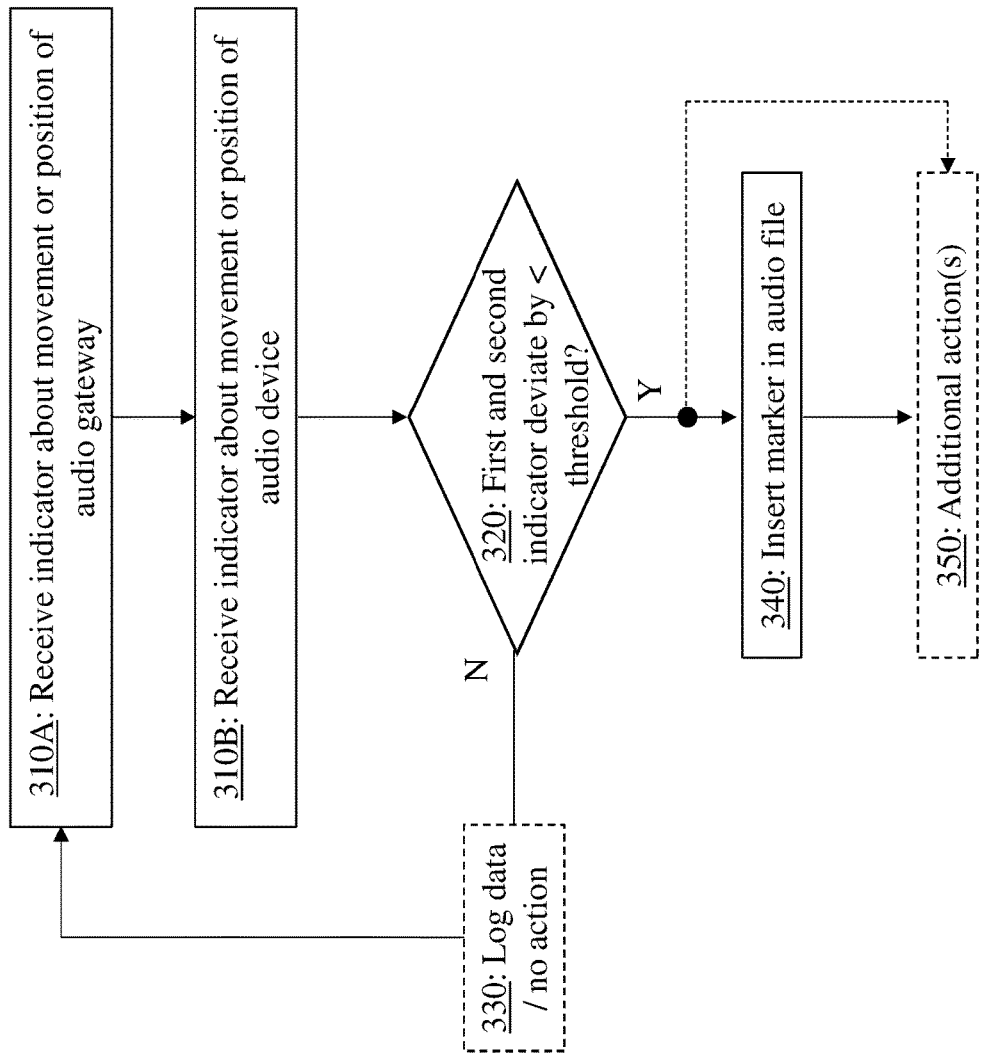
FIG. 3 is a flow diagram illustrating a method performed by a sleep detection application according to various implementations.

FIG. 3 is a flow diagram illustrating processes in a method according to various implementations. In certain implementations, processes in the flow diagram of FIG. 3 are performed by the sleep detection application 150 running at one or more devices described herein. These processes are described with continuing reference to FIGS. 1 and 2. In some cases, as described herein, processes shown sequentially can be performed simultaneously, or nearly simultaneously. However, in other cases, these processes can be performed in a different order.

In a first process, the sleep detection application 150 is configured to receive a first indicator about movement or a position of the audio gateway 130 over a period (process 310A). In some cases, the first indicator includes a sensor signal from one of the sensors 230 at the audio gateway 130 about a change in orientation (e.g., rotation, tipping) or a change in position (e.g., translation) over a period. In particular cases, the first indicator is a sensor signal from an IMU or other sensor that is triggered by any detected movement or position change. In these cases, the sensors 230 detect probable activity by the user 110 (FIG. 1), such as when the user checks a display or interface on the audio gateway 130, makes a phone call with the audio gateway 130 (e.g., by holding to the ear), walks down the street with the audio gateway 130 in hand, etc.

In various implementations, the period is at least approximately several minutes (e.g., 2-4 minutes). However, in more particular cases, the period is at least approximately 1-2 minutes, 30-60 seconds, or 15-30 seconds. In certain implementations, the sleep detection application 150 includes or otherwise accesses a clock timer or other timing mechanism for tracking the period, e.g., on a continuous or periodic basis. The term "approximately" as used with respect to values herein can allot for a nominal variation from absolute values, e.g., of several percent or less.

In another process, which can occur before, after or approximately simultaneously with process 310A, the sleep detection application 150 is configured to receive a second indicator about movement or a position of the audio device 120 over the period, e.g., the same period as the first indicator (process 310B). In various implementations, the second indicator can be of the same type as the first indicator, for example, a sensor signal from one of the sensors 230 at the audio device 120 about a change in orientation (e.g., rotation, tipping) or a change in position (e.g., translation) over the period. In particular cases, the second indicator is a sensor signal from an IMU or other sensor that is triggered by any detected movement or position change.

In certain implementations, the first indicator and the second indicator each include a plurality of indicators representing a rolling average of the movement or position of the audio gateway 130 and the audio device 120 over the period. That is, in various implementations, the first indicator and the second indicator each include a set of two or more sensor signals that represent a rolling average of the movement or the position of the audio gateway 130 and the audio device 120, respectively, over the period. In certain implementations, the sleep detection application 150 averages the sensor signals from each of the audio gateway 130 and the audio device 120 over the period to calculate a rolling average, e.g., average sensor signals over rolling 30 second, one minute, or two minute period(s). In some cases, the sleep detection application 150 calculates the rolling average of the sensor signals from each of the audio gateway 130 and the audio device 120 as long as the sleep detection application 150 is active (i.e., running). In certain implementations, the sleep detection application 150 is activated in response to detecting playback of an audio file at the audio device 120, e.g., in response to detecting activity by an audio playback system, an audio streaming application or other service, and/or playback of an audio file from a data store. It is understood that the sleep detection application 150 can be activated in response to detecting other device functions, e.g., in order to detect the user's sleep state and perform additional functions such as conserve battery life.

As noted herein, the audio device 120 and the audio gateway 130 are separate devices, that is, physically separate devices. As such, the audio device 120 and the audio gateway 130 should provide distinct indicators about movement or position when the user 110 is in motion or otherwise engaging in activities involving one or both devices. The sleep detection application 150 is configured to continuously compare the first indicator and the second indicator to detect a deviation between these indicators (Decision 320, FIG. 3). When the first and second indicators deviate significantly, for example, by a value that is equal to or greater than a threshold, this indicates that the user 110 is moving (e.g., walking, running, cycling, shifting in a seat). In these cases, as shown in FIG. 3, the sleep detection application 150 is configured to continuously receive indicators about the movement or position of the audio device 120 and audio gateway 130, for example, to calculate rolling averages of that sensor data (No to decision 320, or process 330). In particular implementations, the sleep detection application 150 logs the sensor data, but otherwise takes no action.

In contrast, as shown in FIG. 3, when the first and second indicators do not deviate by the threshold amount, this indicates that the user is not moving, and may be asleep or falling asleep. In particular implementations, in response to the first indicator deviating from the second indicator by less than the threshold for the period, the sleep detection application 150 is configured to insert a marker in the audio file (playing at the audio device 120) that enables the user 110 to revert back to the playback at a time of the marker (process 340, FIG. 3). In certain implementations, the sleep detection application 150 includes a timer that is constructed as logic, e.g., executing at the controller 240 in each of the audio device 120 and/or the audio gateway 130. In additional implementations, the timer is constructed as logic executing at only one of the controllers 240, e.g., at the audio device 120 or the audio gateway 130. In other implementations, the timer includes a clock timer connected with the sensor(s) 230 and either integrated into the controller(s) 240 or connected with the controller(s) 240. In response to detecting that the first and second indicators do not deviate by the threshold amount, the sleep detection application 150 triggers the timer to countdown for the period before taking additional action (as noted herein).

In various implementations, as noted herein, the threshold defines approximately synchronized movement or position change between the audio device 120 and the audio gateway 130 such that the user 110 is estimated to be asleep when the first indicator deviates from the second indicator by less than the threshold for the period. That is, the threshold can be equal to a small variation in the sensor data received from the audio device 120 and the audio gateway 130, for example, a variation of less than 20 percent, 15 percent, 10 percent, 5 percent, or 2-3 percent. In some particular cases, the threshold is equal to approximately a 10 percent or a 5 percent variation in the sensor data received from sensor(s) 230 at the audio device 120 as compared with sensor(s) 230 at the audio gateway 130. In certain implementations, the sleep detection application 150 adjusts the threshold based on a detected magnitude of the sensor data from the sensors 230 at the audio device 120 and the audio gateway 130. That is, in some cases, the sleep detection application 150 increases the threshold (e.g., from 5 percent variation up to 10 percent variation) in response to the detected magnitude of sensor signals from all sensors 230 (e.g., at both audio device 120 and audio gateway 130) falling below an activity threshold. In these cases, the sleep detection application 150 reduces the sensitivity to movement or position change as less overall movement or position change is detected. In certain cases, this can help account for inadvertent movement while a user sleeps, such as from twitching, shifting or startling. As noted herein, in particular cases, the period over which the indicators are compared is sufficient to minimize false positives, and can be at least approximately 30 seconds, or in some cases, one or more minutes.

In various implementations, the marker that is placed in the audio file indicates the time in the playback of the audio file at which the movement or position of the audio gateway 130 and the movement or position of the audio device 120 are approximately in sync. That is, the sleep detection application 150 places the marker at a time in the audio file where detected variation in movement/position of the audio device 120 and audio gateway 130 (e.g., via sensor data) is nominal, for example, less than several percent and in some cases less than two or three percent. When variation in the movement or position of these devices is that small, the sleep detection application 150 infers that the user 110 is asleep or falling asleep.

The marker enables the user 110 to quickly revert back to the time in the audio file where the sleep detection application 150 inferred that the user 110 fell asleep (or began the process of falling asleep). In various implementations, the sleep detection application 150 is configured to prompt the user 110 about the marker at a time after placing the marker in the audio file. For example, the sleep detection application 150 can place a notification in a queue, on a display or interface (e.g., at the audio device 120 and/or audio gateway 130), or provide a haptic notification (e.g., vibrational notification) that indicates a marker has been placed in the audio file for the user 110 to revert to playback at an earlier time in the file. In other cases, the sleep detection application 150 provides an audio notification such as a tone, chime, or voice notification about the availability of a marker in the audio file. In some cases, the sleep detection application 150 continues to receive indicators from the sensors 230 at each of the audio device 120 and the audio gateway 130 after placing the marker at the specified time in the audio file. In these cases, the sleep detection application 150 is configured to send the notification about the marker (e.g., via audio prompt, visual prompt, haptic prompt, etc.) in response to detecting that the indicators deviate by an amount greater than the threshold, for example, indicating that the user 110 is now awake. In such cases, the sleep detection application 150 notifies the user 110 about the marker in the audio file after detecting that the user is likely awake again.

As shown in FIG. 3, in optional implementations, the sleep detection application 150 is also configured to perform additional action(s), either after inserting the marker in the audio file, or in place of inserting the marker in the audio file (process 350, optional implementation denoted by node). In some of these cases, the user 110 defines the additional actions as preferences in settings within the sleep detection application 150. For example, the user 110 can define which additional actions should be performed based upon a number of factors, e.g., time of day, day of the week, location, frequency of sleep detection, etc. However, one or more additional action(s) can also be performed in default mode for the sleep detection application 150.

In some particular applications, the sleep detection application 150 is configured to switch playback of the audio file to a distinct audio file in response to the first indicator deviating from the second indicator by less than the threshold. In certain cases, the distinct audio file includes a white noise audio file or a sleep track. In these cases, the sleep detection application 150 pauses playback of the primary audio file (e.g., long form audio content) and switches playback to another sleep-related audio file such as a white noise audio file or a sleep track. In certain cases, the sleep detection application 150 switches the audio files while still inserting the marker in the primary audio file, which can enable the user 110 to efficiently resume playback of that primary audio file after waking.

In additional particular cases, the sleep detection application 150 is run during playback of relaxation-based long form audio content such as a meditation audio, calming guides or sleep aid audio. In these cases, the sleep detection application 150 is configured to perform additional actions based on the user's inferred sleep state. For example, in response to detecting that the user 110 is likely sleeping, or beginning to sleep, while meditation audio is playing at the audio device 120, the sleep detection application 150 increases the volume of the meditation audio, changes the meditation narration, or plays a chime or other audio to gently awake the user 110 from sleep. Alternatively, the sleep detection application 150 pauses or otherwise terminates playback of the meditation audio in response to detecting that the user 110 is likely sleeping or beginning to sleep while meditation audio or calming guide audio is playing at the audio device 120. In still further implementations, the sleep detection application 150 switches playback (as described herein) to another audio steam or track in response to detecting that the user 110 is likely sleeping or beginning to sleep during playback of sleep aid audio. For example, the sleep detection application 150 can switch playback to a different sleep stream or sleep track in response to inferring that the user 110 is asleep, e.g., a sleep track at a lower volume or different rhythm. In some of these cases, the sleep detection application 150 can receive additional and/or distinct data from the sensors 230 (FIG. 2) about user 110 activity to infer a sleep state and/or verify a sleep state during playback of relaxation-based long form audio, e.g., additional motion sensors such as optical sensors. In some cases, the sleep detection application 150 adjusts the sensitivity of sleep detection by modifying the threshold during playback of particular audio (e.g., relaxation-based long form audio), or adjusting the frequency with which indicators are calculated. These adjustments can increase the likelihood of detecting a small or sudden movement that could indicate a sleep state, e.g., a sudden nod of the head. In some examples, the sleep detection application 150 increases the sensitivity of sleep detection (i.e., increases the threshold) during playback of relaxation-based long form audio content because the user 110 is likely to move less during playback of this audio content than during playback of other long form audio content such as podcasts, audio books, etc.

In still further implementations, the sleep detection application 150 plays an alarm at the transducer(s) 210 in the audio device 120 in response to detecting that the first indicator deviates from the second indicator by less than the threshold (Yes to decision 320). The alarm can be played according to any alarm settings defined by the audio device 120 and/or the audio gateway 130 (e.g., volume and tone settings), and can be played alternatively to, or in addition to, inserting the marker in the audio file. In various implementations, the alarm is played in a manner that is intended to awake the user 110 from sleep.

In still further implementations, the sleep detection application 150 is configured to power down the audio device 120 or disable the application controlling playback of the audio file in response to detecting that the first indicator deviates from the second indicator by less than the threshold (Yes to decision 320). In these cases, the sleep detection application 150 can also insert the marker in the audio file to enable playback at the specified time of inferred sleep, however, in other cases, inserting the marker may not be necessary due to the power down and/or disabling event. That is, in various implementations, powering down the audio device 120 or disabling the application controlling playback of the audio file will cause the audio file to stop playback at approximately the time of inferred sleep. This may render the marker unnecessary in some cases. In particular cases, the sleep detection application 150 initiates a warning to the user 110 that the audio device 120 is powering off. In some cases, the warning can include an audible warning, such as a message (via transducer(s) 210) that the audio device 120 is powering down (e.g., "powering down"). In additional implementations, the message can prompt the user to prevent the power off event. In some cases, the message can prompt a response from the user, e.g., a tactile or other motion-based cue detectable by an interface on the audio device 120 and/or audio gateway 130 (e.g., "powering down; tap twice or shake head to avoid powering down") or a voice cue detectable by a microphone in electronics 170 (e.g., "say 'continue' or 'play' to avoid powering down"). In certain cases, the warning can include a vibration-based warning, such as a vibration of the audio device 120 (which may be controlled using sensor(s) 230 or another accelerometer/gyroscope in electronics 160). The sleep detection application 150 can be configured to stop the power off event in response to receiving a cue from the user.

In various particular implementations, the sleep detection application 150 is configured to run on only one of the audio device 120 or the audio gateway 130 (e.g., in a respective controller 240). In these cases, the sleep detection application 150 receives sensor data from sensors 230 at the device on which it is running (e.g., audio device 120), as well as from sensors 230 at the other device (e.g., audio gateway 130), for example, via any communications protocol described herein. In certain cases, the sleep detection application 150 requires only limited processing resources, and as such, can be run on a single device such as the audio device 120.

In any case, the sleep detection application 150 is configured to infer a sleep state of an audio device user, and take one of a variety of actions. That is, the technical effect of the sleep detection application 150 is to control audio device functions based upon an inferred sleep state of the user. In some particular cases, the sleep detection application 150 is configured to infer a sleep state of an audio device user and place a marker in an audio file playing at the audio device to enable the user to resume playback of that file at a desired time. As such, the sleep detection application 150 can enhance the user experience with respect to long form audio content (e.g., audio files or streams), enabling users to efficiently listen to content on demand. In still further implementations, the sleep detection application 150 is configured to control audio playback and/or device functions during playback of relaxation-based long-form audio content, e.g., based on the user's inferred sleep state.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the functions can be performed by one or more programmable processors executing one or more computer programs to perform the functions of the calibration process. All or part of the functions can be implemented as, special purpose logic circuitry, e.g., an FPGA and/or an ASIC (application-specific integrated circuit). Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

Elements of figures are shown and described as discrete elements in a block diagram. These may be implemented as one or more of analog circuitry or digital circuitry. Alternatively, or additionally, they may be implemented with one or more microprocessors executing software instructions. The software instructions can include digital signal processing instructions. Operations may be performed by analog circuitry or by a microprocessor executing software that performs the equivalent of the analog operation. Signal lines may be implemented as discrete analog or digital signal lines, as a discrete digital signal line with appropriate signal processing that is able to process separate signals, and/or as elements of a wireless communication system.

When processes are represented or implied in the block diagram, the steps may be performed by one element or a plurality of elements. The steps may be performed together or at different times. The elements that perform the activities may be physically the same or proximate one another, or may be physically separate. One element may perform the actions of more than one block. Audio signals may be encoded or not, and may be transmitted in either digital or analog form. Conventional audio signal processing equipment and operations are in some cases omitted from the drawings.

In various implementations, components described as being "coupled" to one another can be joined along one or more interfaces. In some implementations, these interfaces can include junctions between distinct components, and in other cases, these interfaces can include a solidly and/or integrally formed interconnection. That is, in some cases, components that are "coupled" to one another can be simultaneously formed to define a single continuous member. However, in other implementations, these coupled components can be formed as separate members and be subsequently joined through known processes (e.g., soldering, fastening, ultrasonic welding, bonding). In various implementations, electronic components described as being "coupled" can be linked via conventional hard-wired and/or wireless means such that these electronic components can communicate data with one another. Additionally, sub-components within a given component can be considered to be linked via conventional pathways, which may not necessarily be illustrated.

Other embodiments not specifically described herein are also within the scope of the following claims. Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

We claim:

1. A computer-implemented method of controlling playback of an audio file at a wearable audio device, the method performed by a processor in response to execution of program code stored on a non-transitory computer readable medium, wherein when executed, the program code causes the processor to perform processes comprising:
   receiving a first indicator about movement or a position of an audio gateway over a period;
   receiving a second indicator about movement or position of the wearable audio device over the period, wherein the wearable audio device is separate from the audio gateway; and
   in response to the first indicator deviating from the second indicator by less than a threshold for the period, inserting a marker in the audio file that enables a user to revert back to the playback at a time of the marker.

2. The computer-implemented method of claim 1, wherein the marker indicates the time in the playback of the audio file at which the movement or position of the audio gateway and the movement or position of the wearable audio device are approximately in sync.

3. The computer-implemented method of claim 1, wherein the first indicator and the second indicator each comprise a plurality of indicators representing a rolling average of the movement or position of the audio gateway and the wearable audio device over the period.

4. The computer-implemented method of claim 1, further comprising switching playback of the audio file to a distinct audio file in response to the first indicator deviating from the second indicator by less than the threshold, wherein the distinct audio file comprises a white noise audio file or a sleep track.

5. The computer-implemented method of claim 1, wherein the first indicator about movement or position of the audio gateway is received from an inertial measurement unit (IMU) located at the audio gateway, and wherein the second indicator about movement or position of the wearable audio device is received from an IMU located at the wearable audio device, wherein each IMU comprises at least one of: an accelerometer, a gyroscope or a magnetometer.

6. The computer-implemented method of claim 1, further comprising playing an alarm at the wearable audio device in response to the first indicator deviating from the second indicator by less than the threshold.

7. The computer-implemented method of claim 1, further comprising powering down the wearable audio device or disabling an application controlling playback of the audio file in response to the first indicator deviating from the second indicator by less than the threshold.

8. The computer-implemented method of claim 1, wherein the audio gateway comprises a smart device that is configured to be worn or otherwise carried by a user.

9. The computer-implemented method of claim 1, wherein the threshold defines approximately synchronized movement or position change between the wearable audio device and the audio gateway such that the user is estimated to be asleep when the first indicator deviates from the second indicator by less than the threshold for the period.

10. The computer-implemented method of claim 9, wherein the period comprises at least approximately 30 seconds.

11. A wearable audio device comprising:
 a sensor for generating a first indicator about movement or a position of the wearable audio device over a period;
 at least one transducer for playing back an audio file; and
 a controller coupled with the sensor and the at least one transducer, the controller configured to:
  receive the first indicator about movement or the position of the wearable audio device over a period;
  receive a second indicator about movement or a position of an audio gateway in communication with the wearable audio device over the period, wherein the wearable audio device is separate from the audio gateway; and
  in response to the first indicator deviating from the second indicator by less than a threshold for the period, inserting a marker in the audio file that enables a user to revert back to the playback at a time of the marker.

12. The wearable audio device of claim 11, wherein the marker indicates the time in the playback of the audio file at which movement or position of the audio gateway and movement or position of the wearable audio device are approximately in sync.

13. The wearable audio device of claim 11, wherein the first indicator and the second indicator each comprise a plurality of indicators representing a rolling average of the movement or the position of the wearable audio device and the audio gateway over the period.

14. The wearable audio device of claim 11, wherein the controller is further configured to:
 a) switch playback of the audio file to a distinct audio file in response to the first indicator deviating from the second indicator by less than the threshold, wherein the distinct audio file comprises a white noise audio file or a sleep track, or
 b) play an alarm at the transducer in response to the first indicator deviating from the second indicator by less than the threshold.

15. The wearable audio device of claim 11, wherein the sensor for generating the first indicator about movement or the position of the wearable audio device comprises a first inertial measurement unit (IMU), and wherein the second indicator about movement or the position of the audio gateway is received from a second IMU at the audio gateway, wherein each IMU comprises at least one of: an accelerometer, a gyroscope or a magnetometer.

16. The wearable audio device of claim 11, wherein the controller is further configured to power down the wearable audio device or disable an application controlling playback of the audio file in response to the first indicator deviating from the second indicator by less than the threshold.

17. The wearable audio device of claim 11, wherein the audio gateway comprises a smart device that is configured to be worn or otherwise carried by a user,
 wherein the threshold defines approximately synchronized movement between the wearable audio device and the audio gateway such that the user is estimated to be asleep when the first indicator deviates from the second indicator by less than the threshold for the period, and
 wherein the period comprises at least approximately 30 seconds.

18. A system comprising:
 an audio gateway having a first sensor for detecting at least one of motion or a position of the audio gateway; and
 a wearable audio device separate from and communicably coupled with the audio gateway for playing back an audio file sent from the audio gateway, the wearable audio device comprising a second sensor for detecting at least one of motion or a position of the wearable audio device,
 wherein a controller at one of the audio gateway or the wearable audio device is configured to:
  receive a first indicator about movement or the position of the audio gateway over a period;
  receive a second indicator about movement or the position of the wearable audio device over the period; and
  in response to the first indicator deviating from the second indicator by less than a threshold for the period, insert a marker in the audio file that enables a user to revert back to the playback at a time of the marker.

19. The system of claim 18, wherein the audio gateway comprises a smart device that is configured to be worn or otherwise carried by a user,
 wherein the threshold defines approximately synchronized movement between the wearable audio device and the audio gateway such that the user is estimated to be asleep when the indicator deviates from the additional indicator by less than the threshold for the period, and
 wherein the period comprises at least approximately 30 seconds.

20. The system of claim 18, wherein the first sensor comprises a first inertial measurement unit (IMU), and wherein the second sensor comprises a second IMU, wherein each IMU comprises at least one of: an accelerometer, a gyroscope or a magnetometer,
 wherein the marker indicates the time in the playback of the audio file at which movement of the audio gateway and movement of the wearable audio device are approximately in sync, and
 wherein the first indicator and the second indicator each comprise a plurality of IMU indicators representing a rolling average of the movement or position of the audio gateway and the wearable audio device over the period.

* * * * *